US00PP18280P3

(12) United States Plant Patent
Eggleton

(10) Patent No.: US PP18,280 P3
(45) Date of Patent: Dec. 4, 2007

(54) ***LAVANDULA* PLANT NAMED 'WINTER LACE'**

(50) Latin Name: *Lavandula stoechas*
Varietal Denomination: Winter Lace

(76) Inventor: Steven Eggleton, 3 Harris Rd, Wonga Park, Melbourne, Vic (AU), 3115

( * ) Notice: Subject to any disclaimer, the term of this patent is extended or adjusted under 35 U.S.C. 154(b) by 31 days.

(21) Appl. No.: 11/429,112

(22) Filed: May 4, 2006

(65) Prior Publication Data

US 2006/0253947 P1 Nov. 9, 2006

(51) Int. Cl.
*A01H 5/00* (2006.01)

(52) U.S. Cl. ..... Plt./226
(58) Field of Classification Search ..... Plt./226
See application file for complete search history.

(56) References Cited

U.S. PATENT DOCUMENTS

PP16,685 P2 * 6/2006 Koning ..... Plt./226
2006/0253947 P1 * 11/2006 Eggleton ..... Plt./263

OTHER PUBLICATIONS

UPOV ROM GTITM Computer Database 2006/04 Citation for 'Winter Lace'.*

* cited by examiner

*Primary Examiner*—Wendy C. Haas

(57) ABSTRACT

A new cultivar of *Lavandula* plant named 'WINTER LACE' that is characterized by dense mounding habit, early blooming, fragrant grey-green foliage, fragrant violet flower spikes with large mid-violet sterile bracts. These traits set 'WINTER LACE' apart from all other existing varieties of *Lavandula* known to the inventor.

2 Drawing Sheets

Genus: *Lavandula* Species: *stoechas*.
Denomination: 'WINTER LACE'.

BACKGROUND OF THE INVENTION

The present invention relates to a new and distinct cultivar of lavender known botanically as *Lavandula stoechas* and hereinafter referred to by the cultivar name 'WINTER LACE'.

The new *Lavandula* cultivar named 'WINTER LACE' is one individual selection in the Australian lavender 'Lace Series' that resulted from a formal breeding program. The breeding program was established in November 2001 and conducted by the inventor at the inventor's nursery in Victoria, Australia. The inventor, a specialists of the genus *Lavandula,* selected 'WINTER LACE' in September 2003. Selection was based on the criterion of strong commercial sales potential, due to early flowering, hardiness, and strong landscape performance.

'WINTER LACE' is a selection arising from controlled cross-pollination of *Lavandula stoechas* 'Kew Red' (unpatented) as the female parent *Lavandula stoechas* 'Pukehou' (unpatented) as the male parent. Cross-pollination of the parent plants took place in Park Orchards, Victoria, Australia. From this cross a seedling population was raised in February 2002, and grown to flowering maturity in 140 mm containers in September 2002. From these seedlings the final selection was made.

'WINTER LACE' is a perennial suitable for use in the landscape. Cultural requirements include full sun, adequate but not excess water, and well-draining soil. Mature height and breadth is 70 cm. 'WINTER LACE' exhibits dense mounding habit, scented green foliage, and scented violet flower spikes in spring and summer. Sterile bracts are mid-violet in color.

The traits that distinguish 'WINTER LACE' from all other *Lavandula* known to the inventor, are early flowering, large sterile bract size, dense plant habit, medium peduncle length, and mid-violet sterile bract color. 'WINTER LACE' is distinguishable from the female parent by length and color of sterile bracts. An individual sterile bract of 'WINTER LACE' is long and mid-violet in color when compared to the sterile bract of 'Kew Red', which is short and pink. 'WINTER LACE' is distinguishable from the male parent by medium peduncle length, dense habit and dark mid-violet sterile bracts. In comparison, 'Pukhou' has a long peduncle, medium to sparse plant density, and dark violet sterile bracts.

The new *Lavandula* cultivar named 'WINTER LACE' was first asexually propagated by the inventor in 2003. Asexual propagation was accomplished at the inventor's nursery in Victoria, Australia using tip cuttings. Since that time 'WINTER LACE' has been determined stable, and reproduces true to type in successive generations of asexual propagation.

SUMMARY OF THE INVENTION

The following traits have been repeatedly observed and represent the distinguishing characteristics of the new *Lavandula* cultivar named 'WINTER LACE'. These traits in combination distinguish 'WINTER LACE' from all other existing varieties of *Lavandula* known to the inventor. 'WINTER LACE' has not been tested under all possible conditions and phenotype differences may be observed with variations in environmental, climatic, and cultural conditions, without however, any variance in genotype.

1. 'WINTER LACE' exhibits dense mounding habit.
2. 'WINTER LACE' exhibits large scented violet flower spikes with mid-violet sterile bracts.
3. 'WINTER LACE' exhibits fragrant grey-green foliage.

3. 'WINTER LACE' is one selection in the Australian lavender 'Lace Series' which offers early bloomers with strong landscape performance.
4. Cultural requirements for 'WINTER LACE' are full sun, adequate but not excess water and well-draining soil.
5. 'WINTER LACE' blooms in spring and summer.
6. 'WINTER LACE' is 70 cm in height and 70 cm in width at maturity.
7. 'WINTER LACE' is asexually propagated utilizing the method of tip and stem cuttings.
8. 'WINTER LACE' is suitable for use as an ornamental in the landscape.
9. 'WINTER LACE' is hardy to USDA Zone 8.

BRIEF DESCRIPTION OF THE DRAWINGS

The accompanying drawings illustrate the overall appearance of the new *Lavandula* cultivar named 'WINTER LACE' showing the colors as true as it is reasonably possible to obtain in color reproductions of this type. Color in the drawings may differ from the color values cited in the detailed botanical description, which accurately describe the actual color of the new *Lavandula* variety named 'WINTER LACE'. The drawings were made of 9-month-old plants greenhouse grown in 16 cm containers.

The drawing labeled

The drawing labeled

Figure 1:
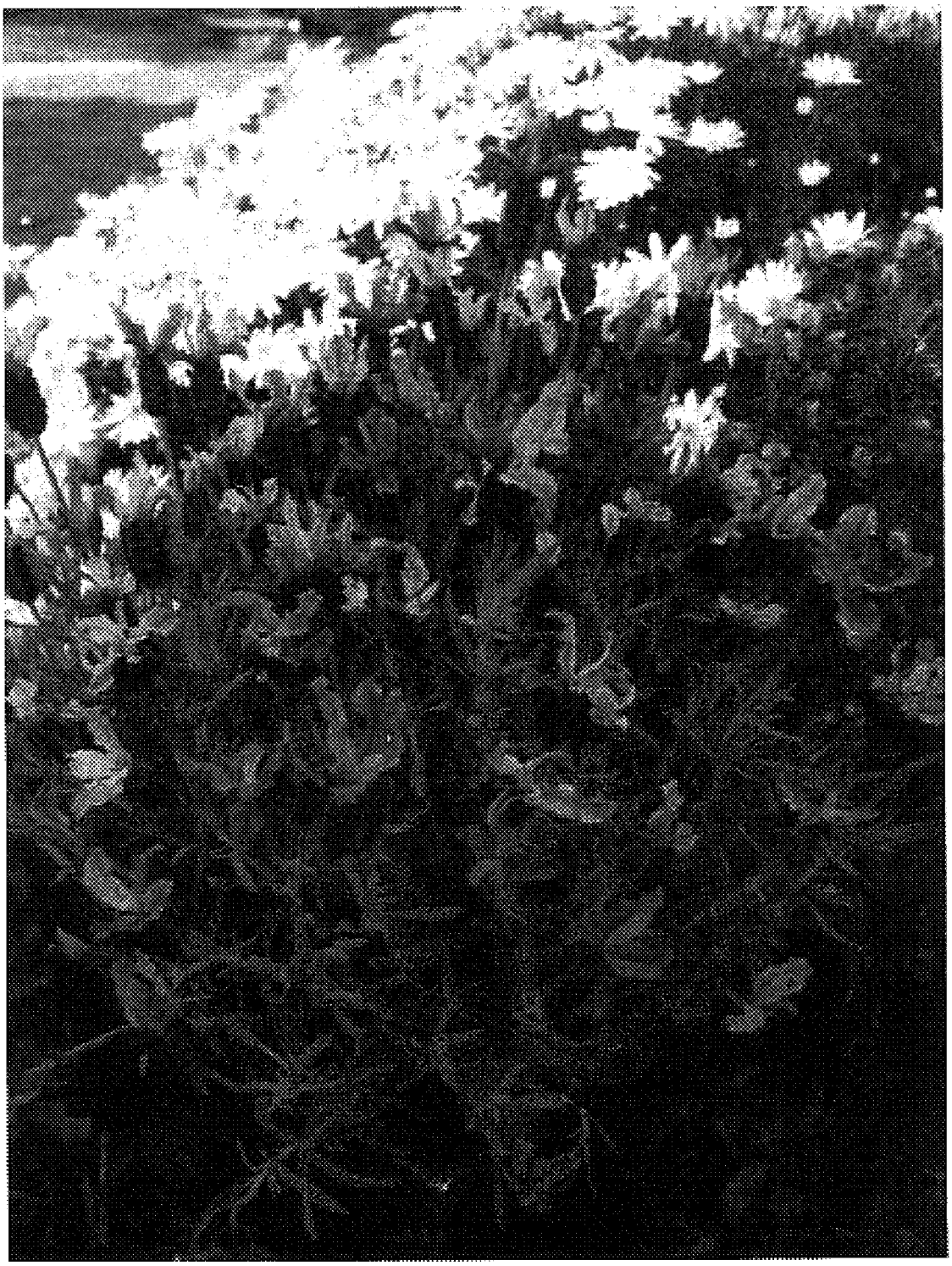
FIG. 1 depicts the plant in bloom from a side perspective.
Figure 2:
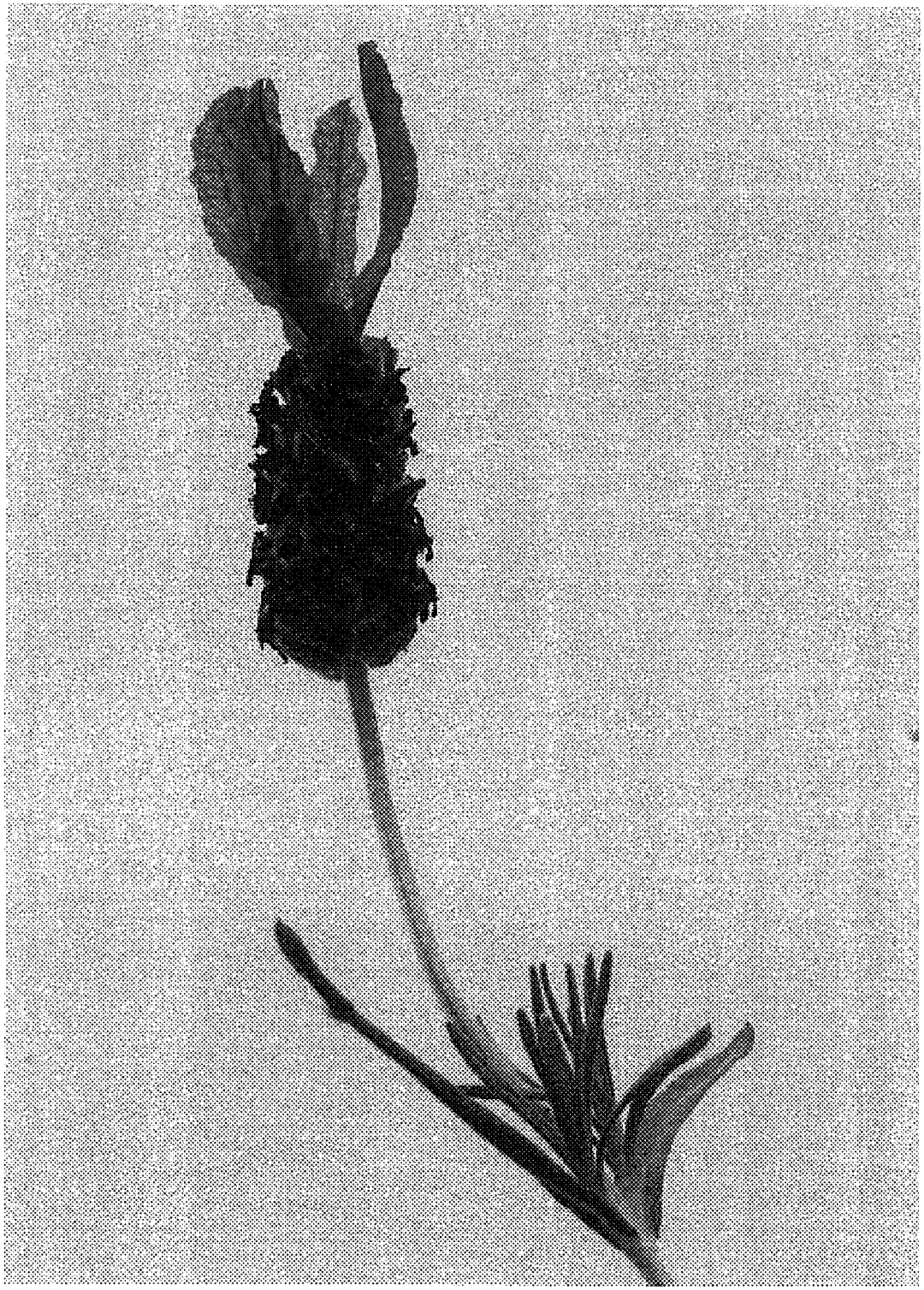
FIG. 2 depicts a close-up view of the flower spike.

Drawings were made using conventional techniques and although the leaf and flower color of 'WINTER LACE' may appear different from the actual color due to light reflectance, they are as accurate as possible by conventional photography.

BOTANICAL DESCRIPTION OF THE PLANT

The following is a detailed botanical description of the *Lavandula* cultivar named 'WINTER LACE'. Data was collected in Arroyo Grande, Calif. from 9-month-old plants greenhouse grown in 16 cm commercial containers. Color determinations are made in accordance with the 2001 Royal Horticultural Society Colour Chart of London, England, except where general color terms of ordinary dictionary significance are used. The growing requirements are similar to the species.

Classification:

*Botanical classification.*—*Lavandula stoechas* 'WINTER LACE'. Family: Lamiaceae.
*Genus.*—*Lavandula.*
*Species.*—*stoechas.*
*Variety denomination.*—'WINTER LACE'.
*Common name.*—Lavender.

Plant:

*Habit.*—Dense and mounding.
*Height* (*at maturity*).—70 cm.
*Width* (*at maturity*).—70 cm.
*Life cycle.*—Perennial.
*Use.*—Ornamental for the landscape.
*Vigour.*—Moderate.
*Hardiness.*—USDA Zone 8.
*Propagation.*—Tip and stem cuttings.
*Root system.*—Fibrous.
*Cultural requirements.*—Full sun, adequate but not excess water, and well-draining soil.
*Time to produce a rooted cutting.*—4–6 weeks.
*Time to produce a 10 cm container plant in bloom.*—20 weeks.
*Seasonal interest.*—Flower spikes in spring and summer.
*Parentage.*—*Lavandula stoechas* 'WINTER LACE' is a selection that resulted from controlled cross-pollination of the following parents: Female parent plant: *Lavandula stoechas* 'Kew Red'. Male parent plant: *Lavandula stoechas* 'Pukehou'.
*Disease and insect resistance or susceptibility.*—Minimal disease and insect susceptibility, with occasional aphids on new growth.

Stem:

*Branching.*—Erect.
*Stem shape.*—Quadrangular.
*Stem surface.*—Tomentose.
*Tomenta color.*—156D.
*Stem color.*—145A.
*Stem length.*—Average is 15 cm.
*Stem width.*—2 mm.
*Stem fragrance.*—Resinous scent.
*Internode length.*—Range of 1.5 cm–2.0 cm.

Foliage:

*Leaf arrangement.*—Opposite.
*Leaf division.*—Simple.
*Leaf shape.*—Linear.
*Leaf margin.*—Entire.
*Leaf apex.*—Apiculate.
*Leaf base.*—Attenuate.
*Leaf attachment.*—Sessile.
*Leaf color* (*adaxial surface*).—189A.
*Leaf color* (*abaxial surface*).—191A.
*Leaf surface* (*adaxial and abaxail surface*).—Tomentose.
*Tomenta color.*—156D.
*Venation.*—Prominent mid-vein observed.
*Vein color* (*adaxial surface*).—189A.
*Vein color* (*abaxial surface*).—191A.
*Leaf length.*—Average is 4.50 cm.
*Leaf width.*—Average is 0.75 cm.
*Leaf fragrance.*—Resinous scent.

Inflorescence:

*Fragrance.*—Resinous scent.
*Blooming period.*—April through August.
*Inflorescence type.*—Spike.
*Spike length.*—5.50 cm.
*Spike diameter.*—3.00 cm.
*Spike shape.*—Oblong-obovate.
*Spike quantity.*—Average of 12.
*Peduncle length.*—8 cm.
*Peduncle width.*—3 mm.
*Peduncle shape.*—Quadrangular.
*Peduncle color.*—194A and N187B are individually present.
*Peduncle surface.*—Tomentose.
*Tomenta color.*—156D. (individual flower is referred to as corolla)
*Corolla number.*—Average of 60 per individual spike.
*Corolla color.*—N92A.
*Corolla shape.*—Salverform.
*Corolla depth.*—9 mm.
*Corolla diameter.*—4 mm.
*Corolla tube depth.*—7 mm.

*Corolla tube diameter.*—1.50 mm.
*Petals.*—Four in number.
*Petals fused or unfused.*—Basally fused.
*Petal shape.*—Reinform.
*Petal length.*—1.75 mm.
*Petal width.*—1.90 mm.
*Petal apex.*—Obtuse and emarginated petal apices individually observed on an individual corolla.
*Petal margin.*—Entire.
*Petal surfaces* (*adaxial and abaxial*).—Glabrous.
*Petal color* (*adaxial surface*).—N92A.
*Petal color* (*abaxial surface*).—N92A.
*Calyx color.*—Individual colors 138B and N92A.
*Calyx shape.*—Tubular.
*Calyx surface.*—Lanate.
*Color of hairs.*—155B.
*Calyx length.*—5 mm.
*Calyx width.*—2 mm.
*Sepals.*—Four in number.
*Sepals fused or unfused.*—¾ length fused.
*Sepal apex.*—Acute. (Fertile bract)
*Fertile bract shape.*—Deltoid.
*Fertile bract length.*—0.75 cm.
*Fertile bract width.*—0.75 cm.
*Fertile bract color* (*ventral surface*).—Individual colors N92D and 83B are present on an individual fertile bract.
*Fertile bract color* (*dorsal surface*).—Individual colors N92D and 83B are present on an individual fertile bract.
*Vein pattern.*—Reticulate.
*Vein color* (*ventral and dorsal surfaces*).—N92D.
*Fertile bract apex.*—Aristulate.
*Fertile bract base.*—Truncate.
*Fertile bract surfaces* (*ventral and dorsal*).—Lanate.
*Fertile bract margin.*—Entire. (Sterile bract)
*Sterile bracts.*—Average of 4 per spike.
*Sterile bract appearance.*—Petaloid.
*Sterile bract form.*—Crisped.
*Sterile bract surfaces* (*abaxial and adaxial*).—Combination of pubescent and irridescent.
*Colors of hairs.*—155B.
*Sterile bract shape.*—Pandurate.
*Sterile bract margin.*—Combination of sinuous and entire.
*Sterile bract length.*—Range of 1.00 cm. to 4.00 cm.
*Sterile bract width.*—Range of 1.00 cm. to 1.25 cm.
*Sterile bract apex.*—Broadly acute.
*Sterile bract base.*—Cuneate.
*Sterile bract color* (*adaxial surface*).—Individual colors 83A, and N92D are present on an individual sterile bract.
*Sterile bract color* (*abaxial surface*).—Individual colors 83B, and N92D are present on an individual sterile bract.
*Vein pattern.*—Reticulate.
*Vein color.*—N92D.

Reproductive organs:
*Stamens.*—Four in number.
*Stamen form.*—Adnate to ventral surface of corolla tube.
*Stamen color.*—155C.
*Stamen length.*—4 mm.
*Anther.*—Four.
*Anther color.*—163A.
*Pollen color.*—163C.
*Pollen quantity.*—Moderate.
*Pistil.*—One.
*Pistil length.*—3 mm.
*Pistil color.*—155B.
*Stigma height.*—Less than 0.50 mm.
*Stigma surface.*—Glossy.
*Stigma shape.*—Orbicular.
*Stigma color.*—83A.
*Ovary dimensions.*—Less than 0.50 mm.
*Ovary shape.*—Globose.
*Ovary color.*—138A.
*Ovary position.*—Superior.

Seed: No seed has been observed to date.

It is claimed:

1. A new and distinct variety of *Lavandula* plant named 'WINTER LACE' as described and illustrated herein.

* * * * *